(12) United States Patent
Kiyota et al.

(10) Patent No.: US 11,035,845 B2
(45) Date of Patent: Jun. 15, 2021

(54) OBSERVATION APPARATUS, OBSERVATION METHOD, OBSERVATION SYSTEM, PROGRAM, AND CELL MANUFACTURING METHOD

(71) Applicant: NIKON CORPORATION, Tokyo (JP)

(72) Inventors: Yasujiro Kiyota, Tokyo (JP); Hiroaki Kii, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 16/849,529

(22) Filed: Apr. 15, 2020

(65) Prior Publication Data
US 2020/0240975 A1 Jul. 30, 2020

Related U.S. Application Data

(63) Continuation of application No. 15/319,336, filed as application No. PCT/JP2014/065916 on Jun. 16, 2014, now Pat. No. 10,656,136.

(51) Int. Cl.
*G01N 33/483* (2006.01)
*G01N 15/06* (2006.01)
(Continued)

(52) U.S. Cl.
CPC ......... *G01N 33/4833* (2013.01); *C12M 41/36* (2013.01); *C12M 41/48* (2013.01); *C12Q 1/02* (2013.01); *G01N 15/0227* (2013.01); *G01N 15/06* (2013.01); *G02B 21/36* (2013.01); *G06K 9/0014* (2013.01); *G06K 9/00147* (2013.01); *G06T 7/0012* (2013.01); *G01N 2015/0065* (2013.01); *G01N 2015/0277* (2013.01);
(Continued)

(58) Field of Classification Search
None
See application file for complete search history.

(56) References Cited

U.S. PATENT DOCUMENTS 7,060,445 B1 6/2006 Dunlay et al.
2006/0280352 A1 12/2006 Muschler et al.
(Continued)

FOREIGN PATENT DOCUMENTS

EP 2703494 A1 3/2014
JP 2012-231709 A 11/2012
(Continued)

OTHER PUBLICATIONS

Sep. 9, 2014 International Search Report issued in International Patent Application No. PCT/JP2014/065916.
(Continued)

*Primary Examiner* — James M Anderson, II
(74) *Attorney, Agent, or Firm* — Oliff PLC

(57) ABSTRACT

An observation apparatus includes: an area calculation unit that calculates a colony area based on an image in which a cell colony is captured; a cell number calculation unit that calculates, based on the image, the number of cells included in a target colony of which an area is calculated by the area calculation unit; and a density calculation unit that calculates, based on the area of the target colony calculated by the area calculation unit and the number of the cells included in the target colony calculated by the cell number calculation unit, a density of the cells included in the target colony.

11 Claims, 10 Drawing Sheets

(51) Int. Cl.
  *C12M 1/36* (2006.01)
  *C12M 1/34* (2006.01)
  *C12Q 1/02* (2006.01)
  *G01N 15/02* (2006.01)
  *G02B 21/36* (2006.01)
  *G06K 9/00* (2006.01)
  *G06T 7/00* (2017.01)
  *G01N 15/00* (2006.01)
  *G02B 21/02* (2006.01)

(52) U.S. Cl.
  CPC ...... *G01N 2015/0693* (2013.01); *G02B 21/02* (2013.01); *G06T 2207/10056* (2013.01); *G06T 2207/30024* (2013.01); *G06T 2207/30242* (2013.01)

(56) References Cited

U.S. PATENT DOCUMENTS

| | | | |
|---|---|---|---|
| 2012/0134571 A1* | 5/2012 | Ito | G06T 7/0016 382/133 |
| 2013/0027539 A1* | 1/2013 | Kiyota | C12M 41/36 348/79 |
| 2014/0064594 A1 | 3/2014 | Sugiyama et al. | |
| 2016/0122803 A1 | 5/2016 | Meissner et al. | |

FOREIGN PATENT DOCUMENTS

| | | | | |
|---|---|---|---|---|
| JP | 2014-018186 A | | 2/2014 | |
| JP | 2014018186 A | * | 2/2014 | ......... G01N 33/5005 |

OTHER PUBLICATIONS

Sep. 9, 2014 Written Opinion of the International Searching Authority issued in International Patent Application No. PCT/JP2014/065916.
Feb. 28, 2018 Office Action issued in U.S. Appl. No. 15/319,336.
May 16, 2018 Extended European Search Report Issued in European Patent Application No. 14895042.1.
May 29, 2018 Office Action Issued in Japanese Patent Application No. 2016-528672.
Dec. 21, 2018 Office Action issued in Japanese Patent Application No. 2016-528672.
May 30, 2019 Office Action issued in U.S. Appl. No. 15/319,336.
Jun. 27, 2019 Office Action issued in European Patent Application No. 14895042.1.
Nov. 27, 2018 Office Action issued in U.S. Appl. No. 15/319,336.
Sep. 29, 2020 Office Action issued in European Patent Application No. 14895042.1.

* cited by examiner

«OBSERVATION APPARATUS, OBSERVATION METHOD, OBSERVATION SYSTEM, PROGRAM, AND CELL MANUFACTURING METHOD»

RELATED APPLICATION

The present application is a continuation application of U.S. patent application Ser. No. 15/319,336 filed Feb. 27, 2017, which in turn is a U.S. national stage application of PCT/JP2014/065916 filed Jun. 16, 2014. Each of these prior applications is incorporated herein by reference in their entireties.

TECHNICAL FIELD

The present invention relates to an observation apparatus, an observation method, an observation system, a program, and a cell manufacturing method.

BACKGROUND

In general, a technology of evaluating a cell incubation state is a base technology in a broad range of fields including an advanced medical field such as regenerative medicine and screening of pharmaceutical products. For example, the regenerative medical field includes a process of cell proliferation and cell differentiation in vitro. In the process, in order to manage success and failure of cell differentiation and presence or absence of cell canceration and infection, it is indispensable to accurately evaluate the cell incubation state. As an example, an evaluation method of a cancer cell using a transcription factor as a marker is disclosed (refer to Patent Document 1).

A stem cell such as an ES (Embryonic Stem) cell or an iPS (induced Pluripotent Stem) cell can be substantially infinitely proliferated theoretically while maintaining differentiation pluripotency that the cell can differentiate into substantially all tissues and therefore has been drawing attention in pharmaceutical development and regenerative medical applications.

RELATED ART DOCUMENTS

Patent Documents

[Patent Document 1] U.S. Pat. No. 7,060,445

SUMMARY OF INVENTION

Problems to be Solved by the Invention

When such a stem cell is applied to drug discovery research or regenerative medicine, it is necessary to incubate a stem cell having a good state (the size of a colony is a moderate size, and the density of a cell that is present in the colony is a moderate density), and therefore, it is required to accurately determine the maturity degree of a cell line during incubation. However, in the related art, the maturity degree of a cell line is determined according to visual observation of a researcher, and therefore, there is a problem that it is impossible to improve the determination accuracy of the maturity degree of a cell line.

In view of the foregoing, a problem to be solved by the present invention is to provide an observation apparatus, an observation method, an observation system, a program, and a cell manufacturing method capable of improving the determination accuracy of the maturity degree of a cell line.

Means for Solving the Problem

[1] In order to solve the problem, an aspect of the present invention is an observation apparatus including: an area calculation unit that calculates a colony area based on an image in which a cell colony is captured; a cell number calculation unit that calculates, based on the image, the number of cells included in a target colony of which an area is calculated by the area calculation unit; and a density calculation unit that calculates, based on the area of the target colony calculated by the area calculation unit and the number of the cells included in the target colony calculated by the cell number calculation unit, a density of the cells included in the target colony.

[2] Further, in order to solve the problem, an aspect of the present invention is an observation system including: an imaging unit that captures an image of a cell during incubation; and an observation apparatus described above.

[3] Further, in order to solve the problem, an aspect of the present invention is an observation method including: an area calculation step of calculating a colony area based on an image in which a cell colony is captured; a cell number calculation step of calculating, based on the image, the number of cells included in a target colony of which an area is calculated according to the area calculation step; and a density calculation step of calculating, based on the area of the target colony calculated according to the area calculation step and the number of the cells included in the target colony calculated according to the cell number calculation step, a density of the cells included in the target colony.

[4] Further, in order to solve the problem, an aspect of the present invention is a program that causes a computer to execute: an area calculation step of calculating a colony area based on an image in which a cell colony is captured; a cell number calculation step of calculating, based on the image, the number of cells included in a target colony of which an area is calculated according to the area calculation step; and a density calculation step of calculating, based on the area of the target colony calculated according to the area calculation step and the number of the cells included in the target colony calculated according to the cell number calculation step, a density of the cells included in the target colony.

[5] Further, in order to solve the problem, an aspect of the present invention is a cell manufacturing method including: a cell incubation step of incubating a cell; an area calculation step of imaging a cell colony incubated in the incubation step and calculating a colony area based on a captured image of the colony; a cell number calculation step of calculating, based on the image, the number of cells included in a target colony of which an area is calculated according to the area calculation step; and a density calculation step of calculating, based on the area of the target colony calculated according to the area calculation step and the number of the cells included in the target colony calculated according to the cell number calculation step, a density of the cells included in the target colony.

Advantage of the Invention

According to the present invention, it is possible to improve the determination accuracy of the maturity degree of a cell line.

DESCRIPTION OF EMBODIMENTS

Embodiment

Figure 1:
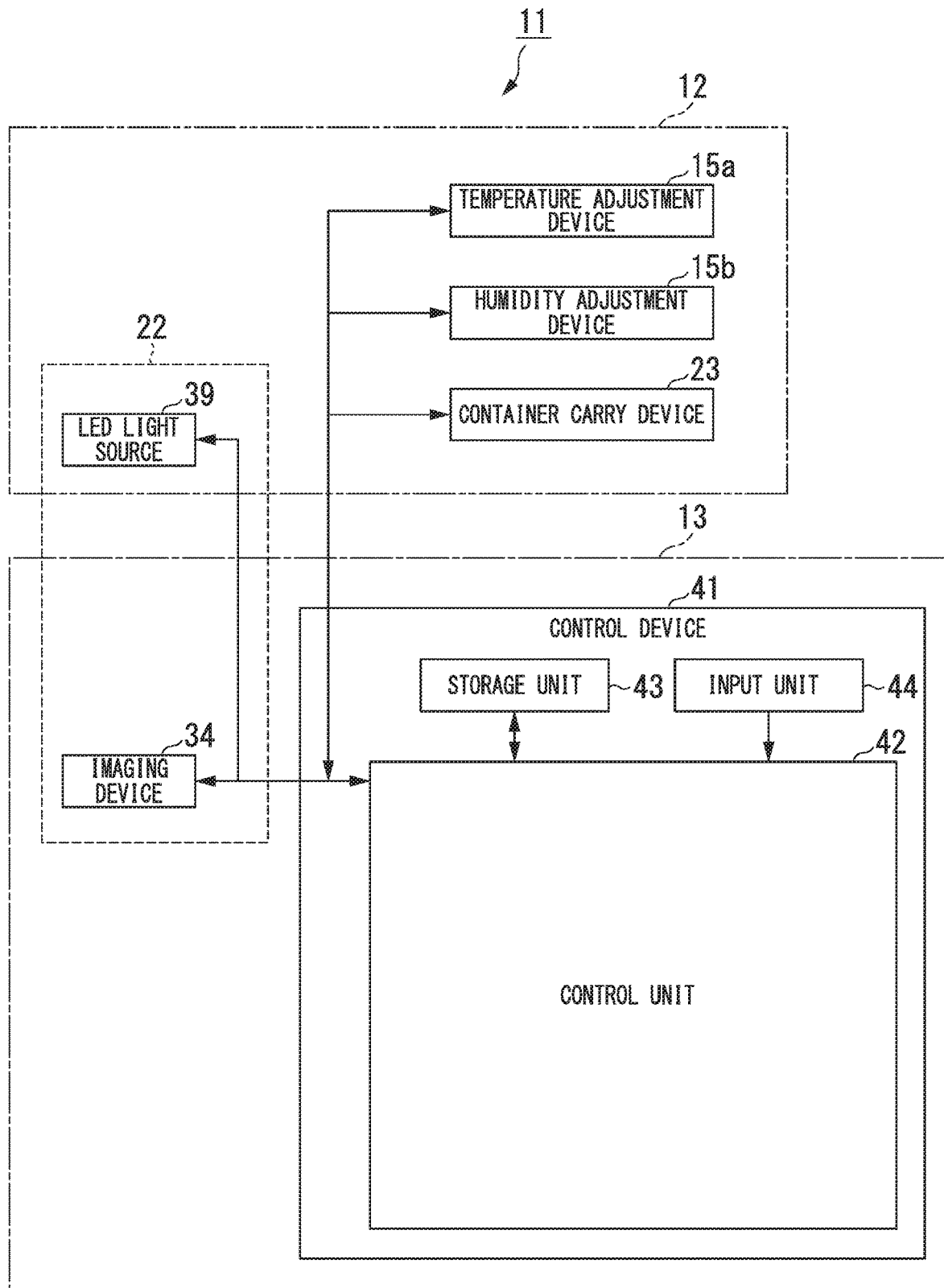
FIG. 1 is a block diagram showing an example of a configuration of an observation apparatus according to an embodiment of the present invention.
Figure 2:
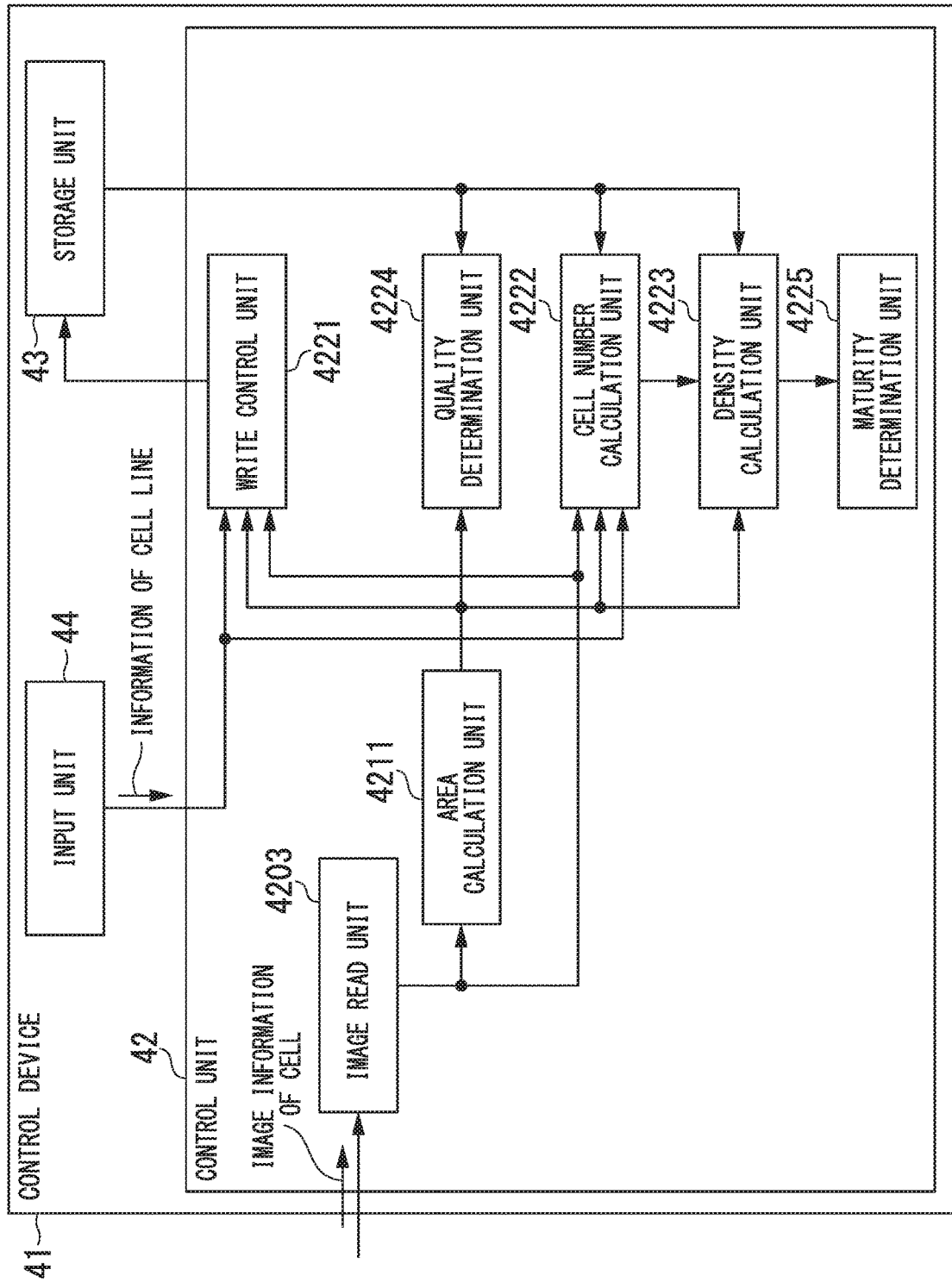
FIG. 2 is a block diagram showing an example of a configuration of a control device included in the observation apparatus of the present embodiment.
Figure 3:
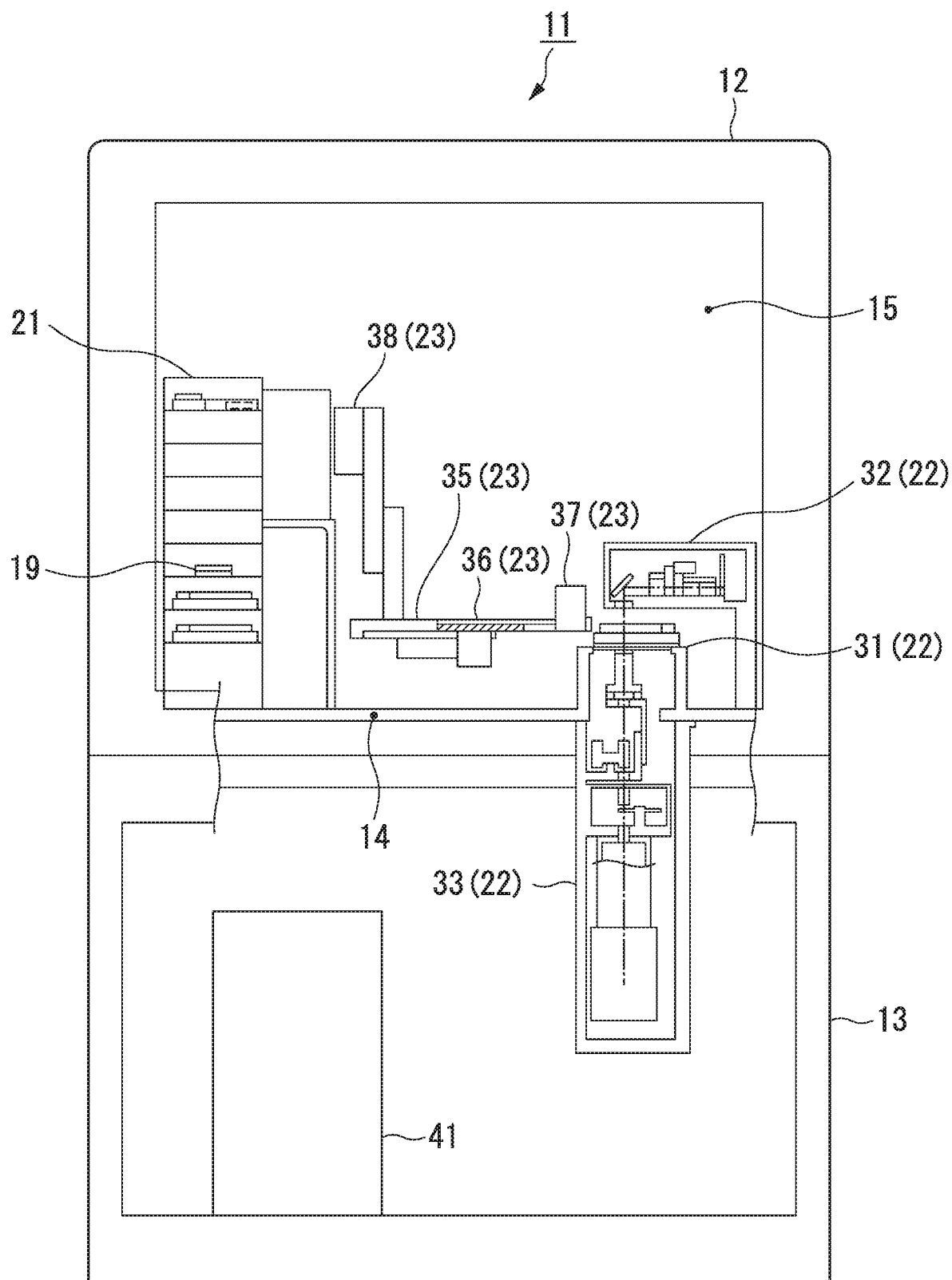
FIG. 3 is a front view of the observation apparatus of the present embodiment.
Figure 4:
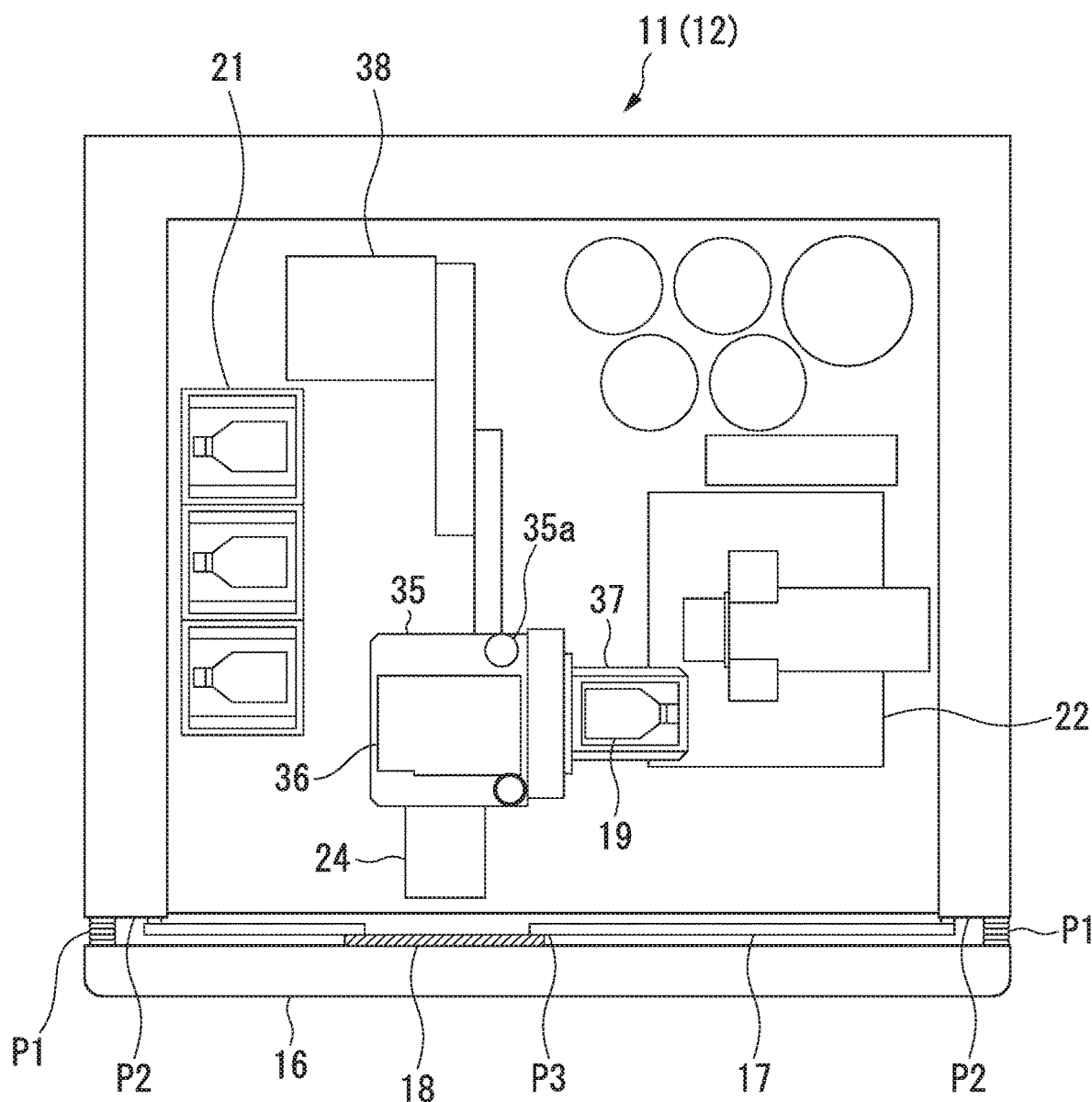
FIG. 4 is a plan view of the observation apparatus of the present embodiment.

Hereinafter, an embodiment of the present invention will be described with reference to the drawings. First, with reference to FIG. 1 to FIG. 4, an outline of a configuration of an incubator (observation apparatus) according to the embodiment of the present invention is described. FIG. 1 is a block diagram showing an example of a configuration of an incubator 11 according to the embodiment of the present invention. FIG. 2 is a block diagram showing an example of a configuration of a control device 41 included in the incubator 11 of the present embodiment. FIG. 3 and FIG. 4 are front and plan views of the incubator 11 of the present embodiment.

The incubator 11 is an apparatus used for incubating a cell and observing the state of the cell by imaging the incubated cell using a microscope camera. The incubator 11 has an upper casing 12 and a lower casing 13. In an assembled state of the incubator 11, the upper casing 12 is arranged above the lower casing 13. The internal spaces of the upper casing 12 and the lower casing 13 are separated in the vertical direction by a base plate 14.

First, an outline of a configuration of the upper casing 12 is described. A constant temperature room 15 in which a cell is incubated is formed inside the upper casing 12. The constant temperature room 15 has a temperature adjustment device 15a and a humidity adjustment device 15b, and the inside of the constant temperature room 15 is maintained to be an environment (for example, an atmosphere at a temperature of 37° C. and a humidity of 90%) suitable for cell incubation (the temperature adjustment device 15a and the humidity adjustment device 15b are not shown in FIG. 3 and FIG. 4).

A large door 16, a medium door 17, and a small door 18 are arranged on the front surface of the constant temperature room 15. The large door 16 covers the front surfaces of the upper casing 12 and the lower casing 13. The medium door 17 covers the front surface of the upper casing 12 and isolates the circumstance of the constant temperature room 15 from the external circumstance when the large door is opened. The small door 18 is attached to the medium door 17 and is a door used for carrying in and out an incubation container 19 in which a cell is incubated. As the incubation container 19 is carried in and out of the small door 18, it is possible to prevent environmental changes in the constant temperature room 15. The airtightness of the large door 16 is maintained by a packing P1, the airtightness of the medium door 17 is maintained by a packing P2, and the airtightness of the small door 18 is maintained by a packing P3.

A stocker 21, an observation unit 22, a container carry device 23, and a carry table 24 are arranged in the constant temperature room 15. Here, the carry table 24 is arranged in front of the small door 18 and is used to carry in and out the incubation container 19 from the small door 18.

The stocker 21 is arranged on the left side of the constant temperature room 15 when seen from the front surface (lower side of FIG. 4) of the upper casing 12. The stocker 21 has a plurality of shelves, and each shelf of the stocker 21 can store a plurality of incubation containers 19. A cell as a target of incubation together with a culture medium is stored in each of the incubation containers 19. The stocker 21 is not essential.

The observation unit 22 is arranged on the right side of the constant temperature room 15 when seen from the front surface of the upper casing 12. A time lapse observation of a cell in the incubation container 19 can be performed using the observation unit 22.

The observation unit 22 is arranged to be fitted in an opening part of the base plate 14 of the upper casing 12. The observation unit 22 has a sample table 31, a stand arm 32 that projects above the sample table 31 and on which an illumination light source is arranged, and a main body part 33 that includes an observation system and an imaging device 34. The sample table 31 and the stand arm 32 are arranged in the constant temperature room 15. On the other hand, the main body part 33 is stored in the lower casing 13.

The sample table 31 is formed of a translucent material, and the incubation container 19 can be arranged on the sample table 31. The sample table 31 is configured to be movable in the horizontal direction and can adjust the position of the incubation container 19 arranged on the upper surface of the sample table 31. The stand arm 32 includes a LED light source 39. The imaging device 34 images, via a microscope optical system, a cell in the incubation container 19 that is illuminated according to transmission illumination from the upper side of the sample table 31 by the stand arm 32 and thereby can obtain a microscope image of the cell.

The container carry device 23 is arranged at the center of the constant temperature room 15 when seen from the front surface of the upper casing 12. The container carry device 23 exchanges the incubation container 19 among the stocker 21, the sample table 31 of the observation unit 22, and the carry table 24. When the stocker 21 is not provided as described above, the container carry device 23 is also unnecessary.

As shown in FIG. 4, the container carry device 23 has a vertical robot 38 having a multijoint arm, a rotation stage 35, a mini stage 36, and an arm unit 37. The rotation stage 35 is attached rotatably by 180° in the horizontal direction to the front end part of the vertical robot 38 via a rotation shaft 35a. Therefore, the rotation stage 35 can cause the arm unit 37 to face each of the stocker 21, the sample table 31, and the carry table 24.

The mini stage 36 is attached slidably in the horizontal direction with respect to the rotation stage 35. The arm unit 37 that grips the incubation container 19 is attached to the mini stage 36.

Next, an outline of a configuration of the lower casing 13 is described. The main body part 33 of the observation unit 22 and the control device 41 of the incubator 11 are stored inside the lower casing 13.

The control device 41 is connected to each of the temperature adjustment device 15a, the humidity adjustment device 15b, the observation unit 22, and the container carry device 23. The control device 41 controls overall the units of the incubator 11 in accordance with a predetermined program.

As an example, the control device 41 controls each of the temperature adjustment device 15a and the humidity adjustment device 15b and maintains the inside of the constant temperature room 15 to be a predetermined environmental condition. The control device 41 controls, based on a predetermined observation schedule, the observation unit 22 and the container carry device 23 and automatically performs an observation sequence of the incubation container 19. The control device 41 performs, based on the image acquired in the observation sequence, an incubation state evaluation process in which the incubation state of the cell is evaluated.

[Calibration Curve (First Calibration Curve) Indicating Temporal Change of Cell Colony Area]

Figure 5:
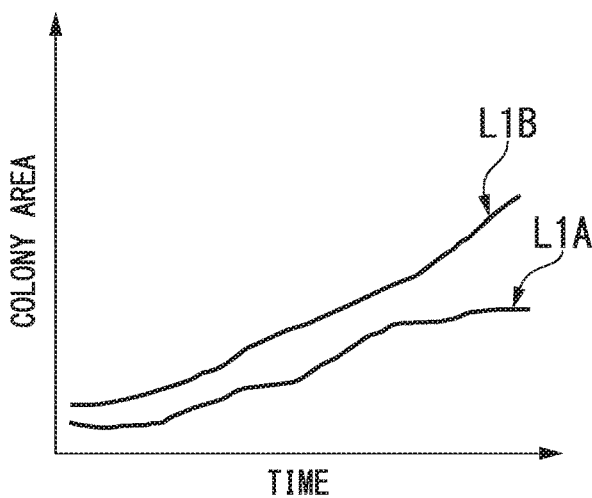
FIG. 5 is a graph showing an example of a temporal change of a colony area for each cell line of the present embodiment.

With reference to FIG. 5, a temporal change of a cell colony area is described.

FIG. 5 is a graph showing an example of a temporal change of a colony area for each cell line. The cells proliferate as time elapses, and therefore, the area of a colony including these cells (hereinafter, simply referred to also as a colony area) increases according to the elapse of time. The temporal change of the colony area differs for each cell line. As an example, the temporal change of the colony area of a cell line A is indicated by a calibration curve L1A in FIG. 5. The temporal change of the colony area of a cell line B is indicated by a calibration curve L1B in FIG. 5. The calibration curve L1A and the calibration curve L1B are collectively referred to as a first calibration curve L1. When the cell line is specified, it is possible to estimate the change of the colony area of a cell line in accordance with the elapse of time based on a predetermined relation shown in FIG. 5, that is, the first calibration curve L1.

By observing the temporal change of the colony area, it is possible to determine whether or not the colony is proliferating normally. That is, when the temporal change amount of the colony area of one colony is larger than a standard temporal change amount of the colony area (for example, when the colony area abnormally increases), there is a possibility that the cell included in this colony differentiates. That is, in a colony of which the colony area abnormally increases, it can be deemed that the cell differentiates, and it is possible to determine that the colony is an abnormal colony. On the other hand, when the temporal change amount of the colony area of one colony is smaller than the standard temporal change amount of the colony area (for example, when the colony area does not temporally change), there is a possibility that the cells included in this colony are dead. That is, in a colony of which the colony area does not temporally change, it can be deemed that the cells are dead, and it is possible to determine that the colony is an abnormal colony. The first calibration curve L1 is registered (stored) in advance for each cell line in the incubator 11 of the present embodiment, and thereby, the incubator 11 determines whether or not the colony is proliferating normally.

[Calibration Curve (Second Calibration Curve) Indicating Relationship Between Cell Colony Area and Cell Number Included in this Colony]

Figure 6:
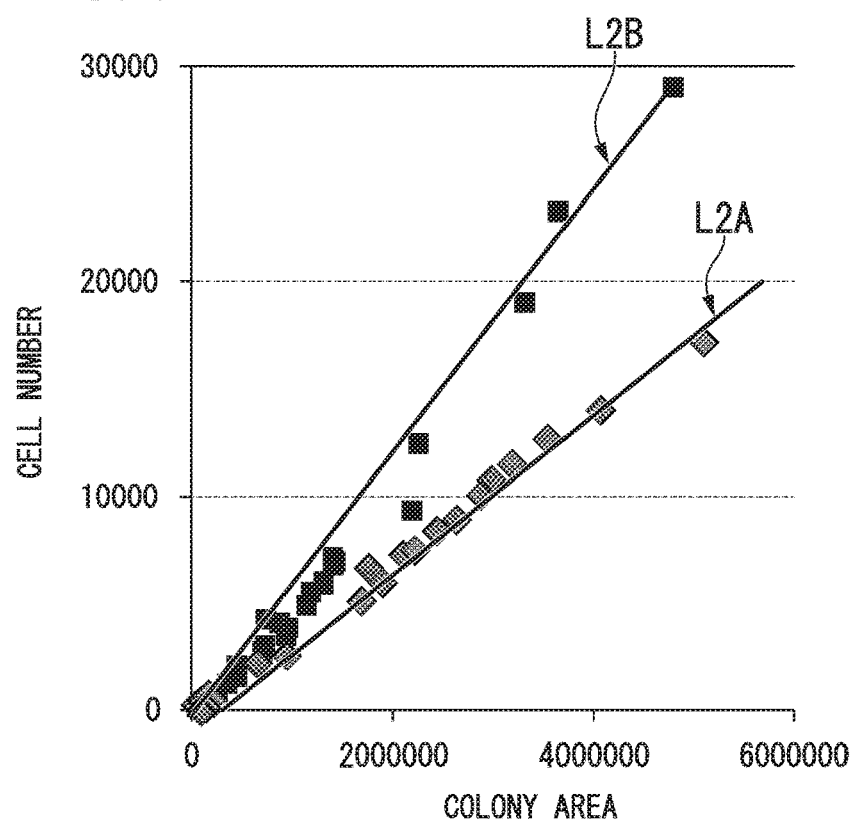
FIG. 6 is a graph showing an example of a relationship between a colony area and a cell number for each cell line of the present embodiment.

With reference to FIG. 6, the relationship between a cell colony area and a cell number is described. The unit of the horizontal axis in FIG. 6 is $\mu m^2$ (micro·square meter), and the unit of the vertical axis is number.

FIG. 6 is a graph showing an example of a relationship between a colony area of one colony for each cell line (hereinafter, colony area) and a cell number in one colony (hereinafter, colony cell number). The user selects a colony suitable for a calibration curve in appearance as a colony which is a target when a calibration curve is prepared. The point of selection is, for example, that a colony which is not adhered to another colony and which is present independently as an individual colony is preferable. The colony size is visually determined, and a wide variety of colonies from a colony having a small colony size to a colony having a large colony size are selected. Such selection may be performed visually according to user's determination, or automatic determination also can be made according to an image analysis by storing the selection condition in advance.

There is a predetermined relationship between a cell colony area and a cell number included in the colony. The predetermined relationship differs for each cell line. As an example, the relationship between the colony area of a cell line A and the cell number included in the colony is indicated by a calibration curve L2A in FIG. 6. The relationship between the colony area of a cell line B and the cell number included in the colony is indicated by a calibration curve L2B in FIG. 6. The calibration curve L2A and the calibration curve L2B are collectively referred to as a second calibration curve L2. When the cell line is specified, it is possible to estimate the cell number included in the colony from the colony area of the cell line based on the second calibration curve L2 shown in FIG. 6. The second calibration curve L2 is registered (stored) in advance for each cell line in the incubator 11 of the present embodiment, and thereby, the incubator 11 estimates (calculates) the cell number included in the colony from the colony image. Specifically, with respect to a certain cell line, the relationship between the cell number and the colony area is measured based on a phase difference image and a fluorescence image which is an image of a fluorescently-stained cell line. The measured relationship between the cell number and the colony area is stored in advance as the second calibration curve L2.

An image used for measuring the cell number is, for example, an image of a cell in a colony captured in a state where the cell is fluorescently stained. Then, with respect to the acquired image, the cell number of cells indicating a predetermined brightness value is measured. At this time, it is possible to apply a smoothing process with respect to the brightness value data obtained from the image, and based on the data, it is possible to specify the cell indicating the predetermined brightness value as a cell to be counted. By controlling the process level when the smoothing process is performed, it is possible to adjust the sensitivity for specifying the cell.

[Calibration Curve (Third Calibration Curve) Indicating Relationship between Cell Colony Area and Cell Density Included in this Colony]

Figure 7:
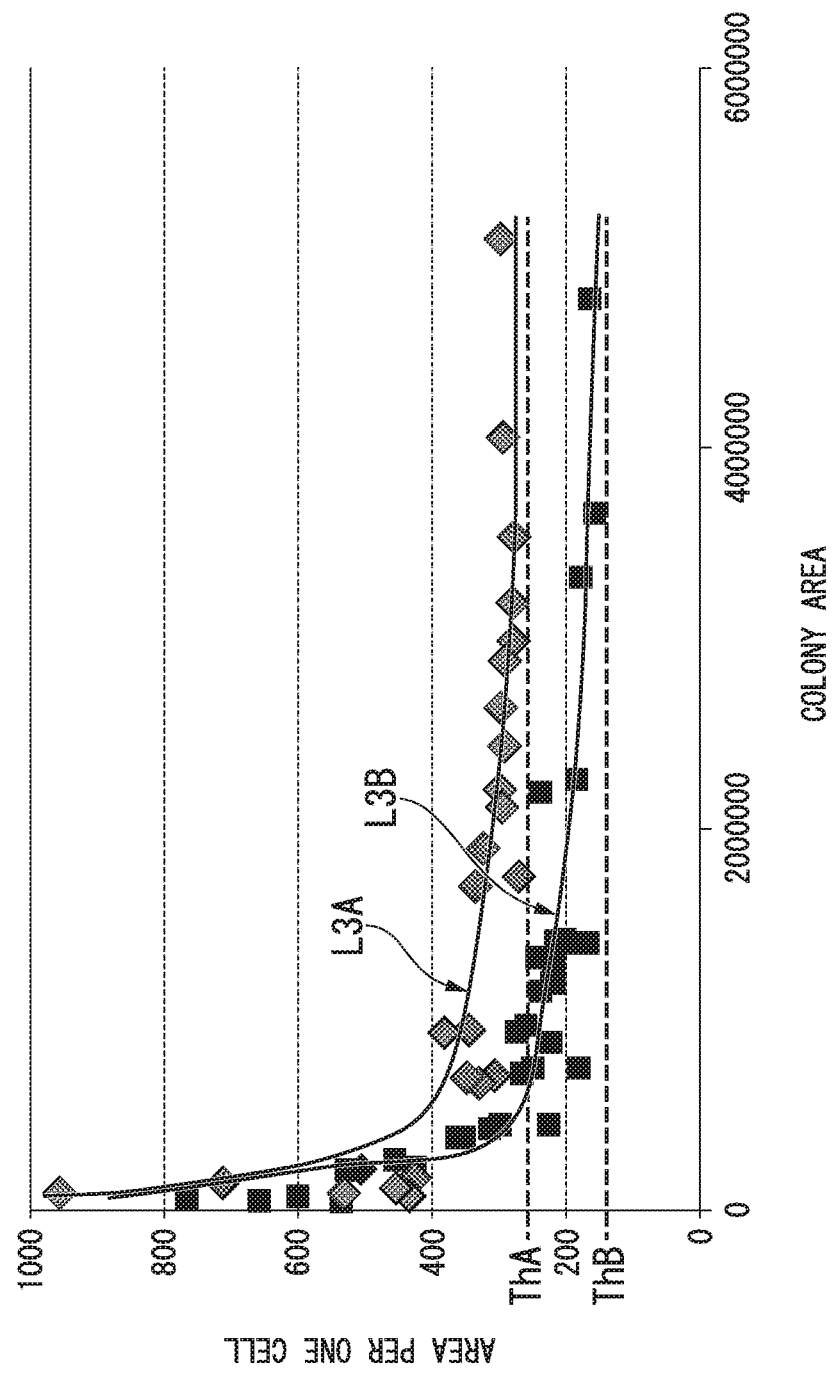
FIG. 7 is a graph showing an example of a relationship between a cell colony area and the density of the cell included in the colony.

With reference to FIG. 7, the relationship between a cell colony area and the density of the cell included in the colony is described.

FIG. 7 is a graph showing an example of a relationship between a cell colony area and the density of the cell included in the colony. The density of the cell included in the colony increases in response to the cell maturity in accordance with the elapse of time. When the cell maturity reaches a certain maturity, the change with the elapse of time of the density of the cell included in the colony is decreased. This means that in accordance with the increase of the colony area, the cell number in the colony is increased, but the change of the area per individual one cell in the colony is decreased.

Accordingly, by observing the density of the cell included in the colony, it is possible to determine the cell maturity.

Specifically, the density of the cell included in the colony is represented by a relationship between the colony area and the area per one cell included in the colony. The colony proliferates over time, and therefore, the colony area increases. When the maturity of the cell included in the colony is increased, the inside of the colony becomes a packed state. That is, when the cell included in the colony is matured, the density of the cell inside the colony is increased. When the cell further proliferates in a state where the inside of the colony is packed, the density of the cell reaches an upper limit to suppress the increase of the density, and the colony area is increased. Accordingly, by observing the temporal change of the density of the cell inside the colony, it is possible to determine the maturity of the cell included in the colony.

The density of the cell included in the colony differs for each cell line. As an example, the relationship between the colony area of a cell line A and the area per one cell included in the colony is indicated by a calibration curve L3A in FIG. 7. The relationship between the colony area of a cell line B and the area per one cell included in the colony is indicated by a calibration curve L3B in FIG. 7. The calibration curve L3A and the calibration curve L3B are collectively referred to as a third calibration curve L3. When the cell line is specified, it is possible to determine the maturity of the cell based on the third calibration curve L3 shown in FIG. 7. Specifically, with respect to the cell line A, when the area per one cell included in the colony reaches a threshold value ThA of the calibration curve L3A shown in FIG. 7, it is determined that the cell line A is matured. With respect to the cell line B, when the area per one cell included in the colony reaches a threshold value ThB of the calibration curve L3B shown in FIG. 7, it is determined that the cell line B is matured.

That is, the third calibration curve L3 is registered (stored) in advance for each cell line in the incubator 11 of the present embodiment, and thereby, the incubator 11 determines the cell maturity from the colony image. Specifically, when a calibration curve is prepared, with respect to a certain cell line, the relationship between the colony area and the density of the cell included in the colony is measured based on a phase difference image and a fluorescence image which is an image of a fluorescently-stained cell line. The measured relationship between the colony area and the density of the cell included in the colony is stored in advance as the third calibration curve L3.

With reference back to FIG. 1, the configuration of the control device 41 is described. The control device 41 has a control unit 42, a storage unit 43, and an input unit 44.

The storage unit 43 is formed of a hard disk, a non-volatile storage medium such as a flash memory, a volatile storage medium such as a DRAM and a SRAM, or the like. Management data regarding each incubation container 19 stored in the stocker 21, data of an entire observation image captured by an imaging device, and data of a microscope image are stored in the storage unit 43. A program executed by the control unit 42 is stored in the storage unit 43. A variety of calculation results by the control unit 42 are temporarily stored in the storage unit 43.

The management data described above includes (a) index data indicating an individual incubation container 19, (b) a storage position of the incubation container 19 in the stocker 21, (c) the type and shape (well plate, dish, flask, or the like) of the incubation container 19, (d) the type (information by which a cell line is identified) of the cell incubated in the incubation container 19, (e) an observation schedule of the incubation container 19, (f) an imaging condition (a magnification of an objective lens, an observation point in the container, or the like) during a time lapse observation, and the like. With respect to the incubation container 19 in which cells can be incubated simultaneously at a plurality of small containers such as a well plate, each of the management data is generated for each of the plurality of small containers.

In the present example, different types of cell lines are observed as the cell line to be observed. In this case, information by which the cell line is identified is required. However, when the cell line which is observed is one cell line, and it is unnecessary to identify the cell line, the cell line identification information is not essential. Even when the cell line which is observed is one cell line, information indicating the cell line may be input.

The colony area and calibration curve information indicating the relationship between the colony area and the number of cells included in the colony are associated with each other and stored in the storage unit 43.

When different types of cell lines are observed, cell line information by which a cell line of a cell is identified is stored in the storage unit 43 and is preferably associated with each of information to be stored. Feature amount information indicating a feature amount of the colony area is stored and is preferably associated with each of information to be stored.

The input unit 44 includes an input device such as a keyboard and a mouse. A variety of information such as cell line information are input to the input unit 44 according to the operation of the user.

Next, with reference to FIG. 2, the configuration of the control unit 42 is described. The control unit 42 includes an image read unit 4203, an area calculation unit 4211, a write control unit 4221, a cell number calculation unit 4222, and a density calculation unit 4223.

In FIG. 2, a case in which it is determined whether the colony is good or bad based on the first calibration curve L1 is supposed, and a configuration in which a quality determination unit 4224 is included is shown. In FIG. 2, a case in which the cell maturity is determined based on the third calibration curve L3 is supposed, and a configuration in which a maturity determination unit 4225 is included is shown. In the incubator 11 of the present embodiment, the quality determination unit 4224 and the maturity determination unit 4225 are not essential.

The control unit 42 is, for example, a processor that performs a variety of calculation processes of the control device 41. The control unit 42 may function as each of the image read unit 4203, the area calculation unit 4211, the quality determination unit 4224, the maturity determination unit 4225, the write control unit 4221, and the cell number calculation unit 4222 by executing a program.

The write control unit 4221 controls writing, in the storage unit 43, of information output by each unit of the control device 41.

The image read unit 4203 reads the image data of the microscope image or the entire observation image captured by the imaging device 34 and supplies the read image data to each unit of the control device 41. The image read unit 4203 reads the image data of the microscope image or the entire observation image stored in the storage unit 43 and supplies the read image data to each unit of the control device 41.

In two cases which are a case in which the first calibration curve L1 is stored in the storage unit 43 and a case in which it is determined whether the colony is good or bad based on the first calibration curve L1 and the colony image captured by the imaging device 34, the area calculation unit 4211 calculates the colony area. Here, first, the case in which the first calibration curve L1 is stored in the storage unit 43 is described, and then, the case in which it is determined whether the colony is good or bad based on the first calibration curve L1 is described.

The area calculation unit 4211 calculates the colony area and causes the storage unit 43 via the write control unit 4221 to store, as calibration curve information, the first calibration curve L1 in which the calculated colony area and the number of cells included in the colony are associated with each other. That is, the area calculation unit 4211 causes the storage unit 43 to store the first calibration curve L1. In case of a plurality of cell lines, the storage unit 43 is caused to store cell line information (cell line ID) via the input unit 44, and the storage unit 43 is caused to store calibration curve information for each cell line.

In case of a plurality of types of cell lines, it is required to input information (cell line ID) indicating a cell line type. With respect to the input of information indicating a cell line type, the user understanding the types of observed cell lines may input the information. Further, by using a technology in which the cell line type is automatically determined using a matching technique or the like of identifying a cell according to the morphology, brightness, and the like of the observed cell, the information indicating a cell line type can be also automatically generated to be input.

In the present example, a case in which the user inputs the information (cell line ID) indicating the cell line via the input unit 44 is described.

The area calculation unit 4211 calculates the colony area based on the image in which the cell colony is captured. A specific example of the image of which the colony area is calculated by the area calculation unit 4211 is described with reference to FIG. 8.

Figure 8:
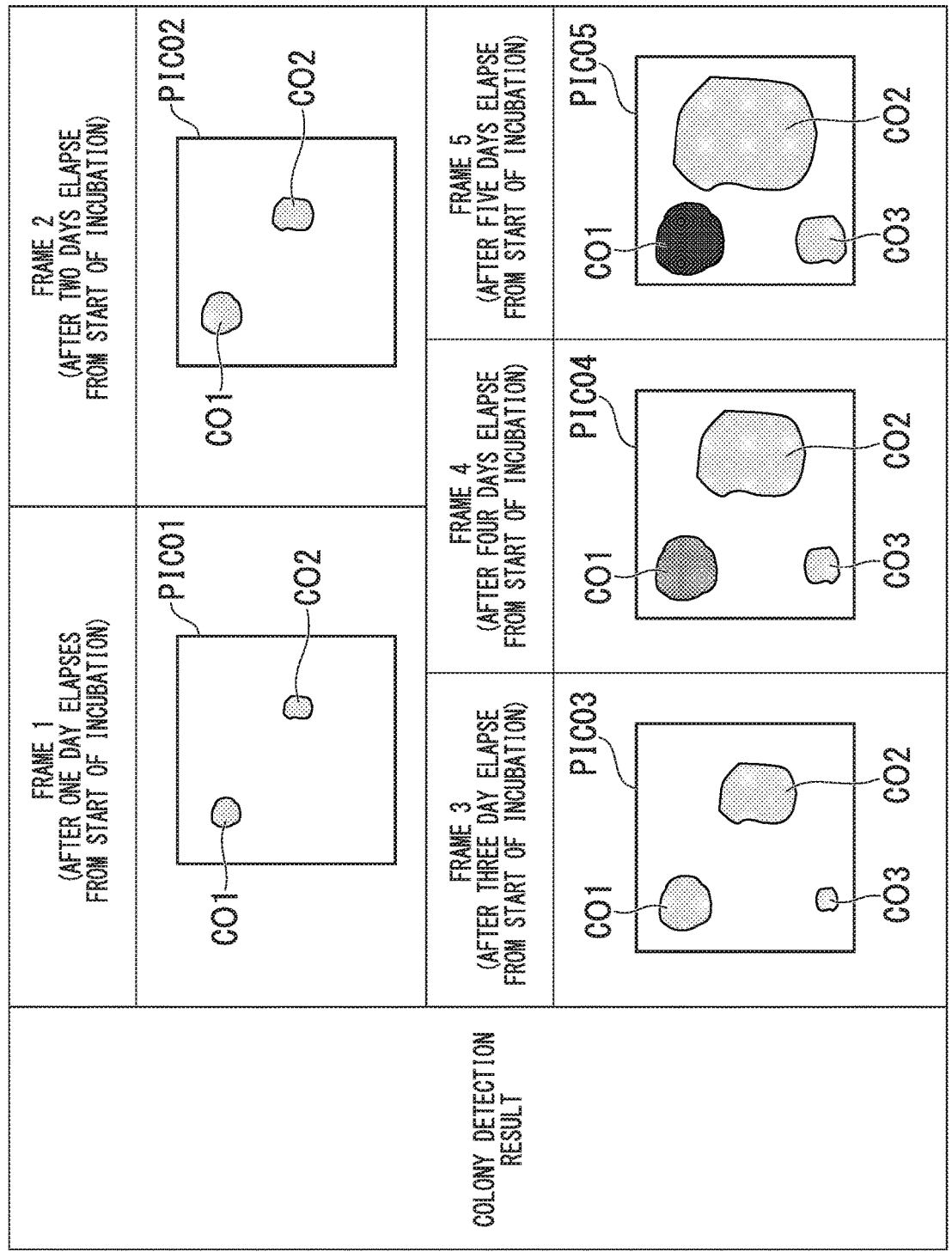
FIG. 8 is a schematic diagram showing an example of an entire observation image captured by an imaging device of the present embodiment.

FIG. 8 is a schematic diagram showing an example of an entire observation image captured by the imaging device 34 of the present embodiment. Among the entire observation image shown in FIG. 8, an entire observation image PIC01 is an image (frame 1) of a colony detection result after one day elapses from the start of incubation. Entire observation image PIC02 to entire observation image PIC05 (frame 1 to frame 5) are images of colony detection results after two to five days elapse from the start of incubation.

The entire observation image PIC01 includes an image of a first colony CO1 and an image of a second colony CO2 after one day elapses from the start of incubation. The entire observation image PIC02 includes an image of the first colony CO1 and an image of the second colony CO2 after two days elapse from the start of incubation. As shown in FIG. 8, the first colony CO1 after two days elapse from the start of incubation proliferates compared to the first colony CO1 after one day elapses from the start of incubation, and the area is increased. As shown in FIG. 8, the second colony CO2 after two days elapse from the start of incubation proliferates compared to the second colony CO2 after one day elapses from the start of incubation, and the area is increased.

The entire observation image PIC03 includes an image of the first colony CO1, an image of the second colony CO2, and an image of a third colony CO3 after three days elapse from the start of incubation. As shown in FIG. 8, the first colony CO1 after three days elapse from the start of incubation proliferates compared to the first colony CO1 after two days elapse from the start of incubation, and the area is increased. As shown in FIG. 8, the second colony CO2 after three days elapse from the start of incubation proliferates compared to the second colony CO2 after two days elapse from the start of incubation, and the area is increased.

The temporal change of the colony area is described by sorting the entire observation image PIC01 to the entire observation image PIC03 in a time series and comparing the images. In this case, the area of the first colony CO1 monotonously increases in the entire observation image PIC01 to the entire observation image PIC03. On the other hand, with respect to the area of the second colony CO2, the increase amount in the entire observation image PIC01 to the entire observation image PIC02 greatly differs from the increase amount in the entire observation image PIC02 to the entire observation image PIC03. That is, the increase amount of the area of the second colony CO2 in the entire observation image PIC02 to the entire observation image PIC03 is larger than the increase amount of the area of the second colony CO2 in the entire observation image PIC01 to the entire observation image PIC02. That is, the area of the second colony CO2 drastically increases after three days elapse from the start of incubation. This indicates that there is a possibility that the second colony CO2 differentiates after three days elapse from the start of incubation and abnormally proliferates.

Figure 9:
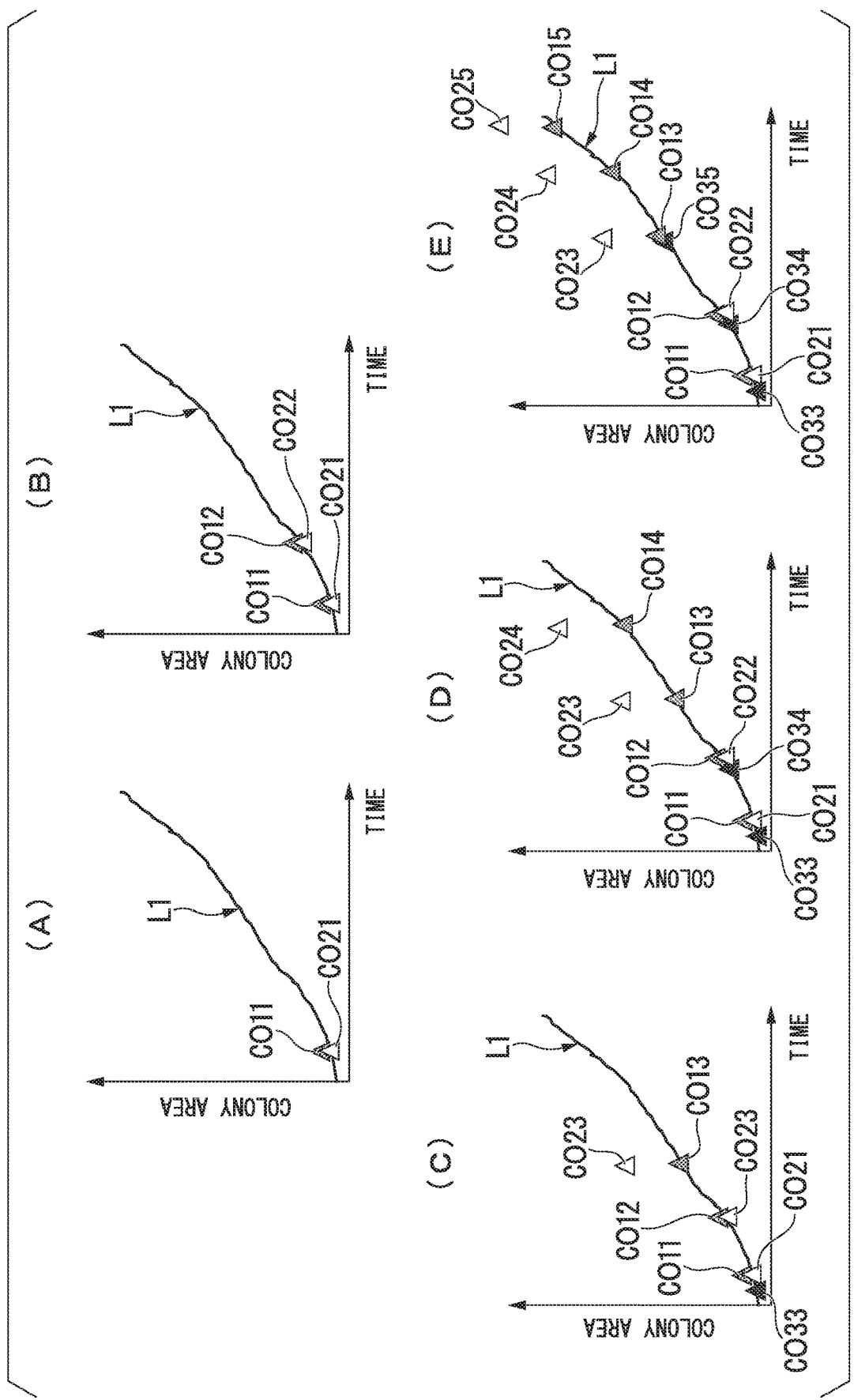
FIG. 9 is a graph showing an example of a relationship between the temporal change of the colony area and a first calibration curve of the present embodiment.

With reference to FIG. 9, the relationship between the temporal change of the colony area and the first calibration curve is described.

FIG. 9 is a graph showing an example of the relationship between the temporal change of the colony area and the first calibration curve of the present embodiment. In FIG. 9, the horizontal axis represents time, and the vertical axis represents colony area. FIG. 9(A) shows the area of the colony included in the entire observation image PIC01 obtained by acquiring the image of the colony. That is, FIG. 9(A) shows the area of the first colony CO1 and the area of the second colony CO2 after one day elapses from the start of incubation. As shown in FIG. 9(A), both an area CO11 of the first colony CO1 and an area CO21 of the second colony CO2 are plotted on the first calibration curve L1. That is, after one day elapses from the start of incubation, both the area CO11 of the first colony CO1 and the area CO21 of the second colony CO2 show a normal value.

Each of FIG. 9(B) to (E) shows the area of the colony included in each of the entire observation image PIC02 to the entire observation image PIC05 obtained by acquiring the image of the colony. FIG. 9(B) shows an area CO12 of the first colony CO1 and an area CO22 of the second colony CO2 after two days elapse from the start of incubation. As shown in FIG. 9(B), both the area CO12 of the first colony CO1 and the area CO22 of the second colony CO2 are plotted on the first calibration curve L1. That is, after two days elapse from the start of incubation, both the area CO12 of the first colony CO1 and the area CO22 of the second colony CO2 show a normal value.

FIG. 9(C) shows an area CO13 of the first colony CO1 and an area CO23 of the second colony CO2 after three days elapse from the start of incubation. As shown in FIG. 9(C), the area CO13 of the first colony CO1 is plotted on the first calibration curve L1. On the other hand, the area CO23 of the second colony CO2 is not plotted on the first calibration curve L1. That is, after three days elapse from the start of incubation, the area CO12 of the first colony CO1 shows a normal value, and the area CO23 of the second colony CO2 shows an abnormal value. This indicates that there is a possibility that the second colony CO2 differentiates after three days elapse from the start of incubation and abnormally proliferates. That is, it is possible to determine whether the colony area is a normal value or is an abnormal value based on whether or not the colony area is present on the first calibration curve L1. In this example, since the second colony CO2 is in a state where the colony area is greater than that of a normal colony, and there is a possibility that the second colony CO2 differentiates after three days elapse from the start of incubation and abnormally proliferates, the subsequent incubation of the second colony CO2 is stopped (for example, remove the second colony CO2 from the culture medium).

In the present embodiment, the quality determination unit 4224 determines whether the colony is good or bad. That is, the quality determination unit 4224 determines whether the colony is good or bad based on the change of the colony area according to the elapse of time calculated by the area calculation unit 4211. Specifically, the quality determination unit 4224 determines whether the colony is good or bad based on the colony area calculated by the area calculation unit 4211 and the first calibration curve L1 stored in the storage unit 43.

With reference back to FIG. 8, after three days elapse from the start of incubation, the third colony CO3 that has not been present before arises. This is because an iPS cell is different from an ordinary cell and the timing of adhesion is non-uniform. Specifically, the first colony CO1 and the second colony CO2 adhere and proliferate after one day elapses from the start of incubation. On the other hand, the third colony CO3 does not adhere until two days elapse from the start of incubation and adhere after three days elapse from the start of incubation to start proliferating. In this way, the imaging device 34 generates an entire observation image by imaging multiple times in accordance with the elapse of time from the start of incubation.

An entire observation image PIC04 (frame 4) includes an image of the first colony CO1, an image of the second colony CO2, and an image of the third colony CO3 after four days elapse from the start of incubation. As shown in FIG. 8, the first colony CO1 after four days elapse from the start of incubation proliferates compared to the first colony CO1 after three days elapse from the start of incubation, and the area is increased. As shown in FIG. 8, the second colony CO2 after four days elapse from the start of incubation proliferates compared to the second colony CO2 after two days elapse from the start of incubation, and the area is increased.

That is, the imaging device 34 captures a time lapse image from the start of incubation. Thereby, the incubator 11 of the present embodiment can observe the state of colony with good accuracy even with respect to a cell of which the timing of adhesion is non-uniform such as an iPS cell.

With reference back to FIG. 2, the area calculation unit 4211 acquires the entire observation image captured by the imaging device 34 from the image read unit 4203. The area calculation unit 4211 generates a colony detection result image (the entire observation image PIC01 to the entire observation image PIC05) shown in FIG. 8 based on the entire observation image which was acquired.

The area calculation unit 4211 calculates the colony area of a cell based on the generated colony detection result image. Specifically, the area calculation unit 4211 masks a colony part using an object detection algorithm according to a known learning function, determines the masked part (region surrounded by a curve in the colony detection result image of FIG. 8) as a region where the colony is present, and calculates the colony area from the masked region. The calculation method of the colony area is not limited thereto.

When the user inputs information (cell line ID) indicating a cell line via the input unit 44, the cell number calculation unit 4222 searches calibration curve information stored by the storage unit 43 using the cell line ID as a search key and acquires the second calibration curve L2 (relationship between the colony area and the cell number) which the cell line ID matches based on the search result. The cell number calculation unit 4222 calculates the cell number based on the colony area calculated by the area calculation unit 4211 using the acquired second calibration curve L2. That is, the cell number calculation unit 4222 calculates the number of cells included in the target colony of which the area is calculated by the area calculation unit 4211 based on the image captured by the imaging device 34.

The density calculation unit 4223 calculates the density of cells included in the colony based on the colony area calculated by the area calculation unit 4211 and the number of cells included in the colony calculated by the cell number calculation unit 4222. Specifically, the density calculation unit 4223 calculates the area per one cell included in the colony based on the colony area calculated by the area calculation unit 4211 and the cell number calculated by the cell number calculation unit 4222.

The maturity determination unit 4225 determines the maturity of the cell included in the colony based on the density of the cell calculated by the density calculation unit 4223. Specifically, with respect to the cell line A, when the area per one cell included in the colony reaches the threshold value ThA of the calibration curve L3A shown in FIG. 8, the maturity determination unit 4225 determines that the cell line A is matured. With respect to the cell line B, when the area per one cell included in the colony reaches the threshold value ThB of the calibration curve L3B shown in FIG. 8, the maturity determination unit 4225 determines that the cell line B is matured.

[Operation of Incubator (Observation Apparatus)]

Next, an example of an operation of the incubator 11 is described. The incubator 11 estimates the number of cells included in the colony from the cell colony area based on the registered calibration curve to thereby calculate the number of cells. Here, the calibration curve is information indicating the relationship between the cell colony area and the number of cells included in the colony. First, an operation in which the calibration curve is registered is described, and then, an operation in which the number of cells is calculated based on the registered calibration curve is described.

[Operation of Calibration Curve Registration]

First, an operation of calibration curve registration is described with reference to FIG. 10.

Figure 10:
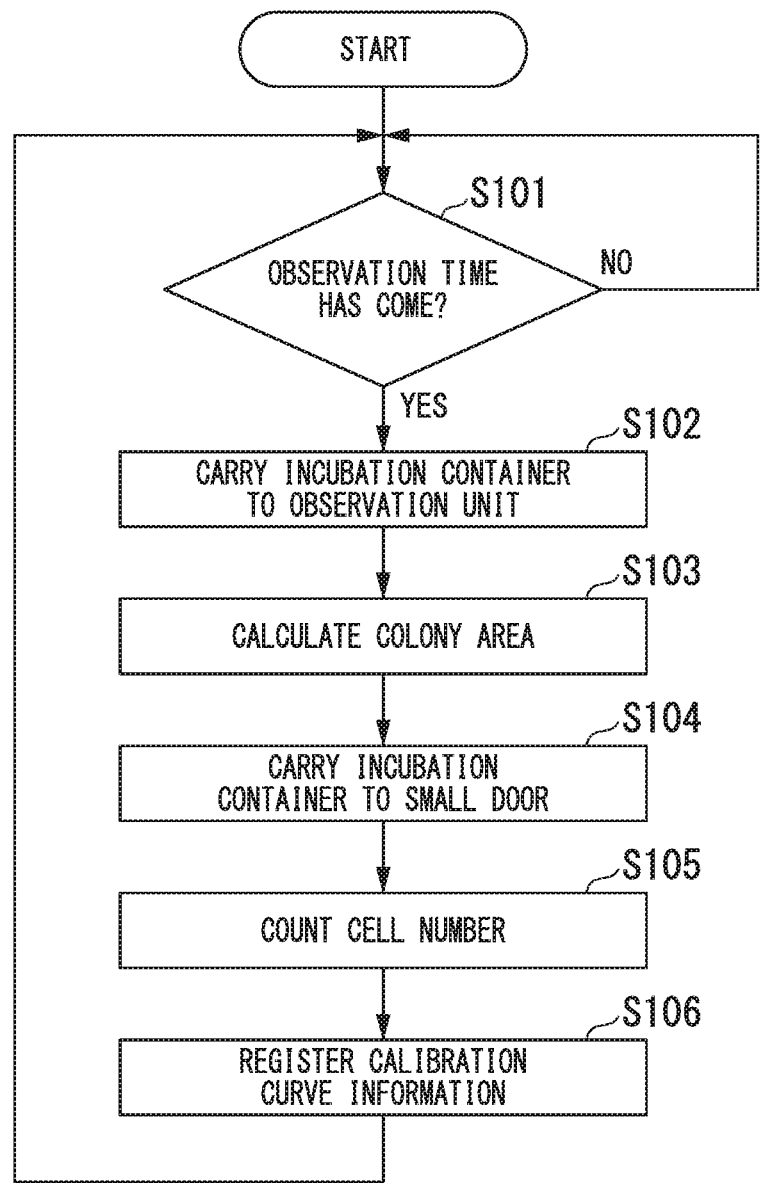
FIG. 10 is a flowchart showing an example of a calibration curve registration operation according to the observation apparatus of the present embodiment.

FIG. 10 is a flowchart showing an example of an operation of calibration curve registration by the incubator 11 (observation apparatus) of the present embodiment. The incubator 11 stores a calibration curve (first calibration curve L1, second calibration curve L2, and third calibration curve L3) for each cell line.

As an example, based on the image data described above, the incubator 11 detects a colony image in the image data and calculates the area of the colony image. The incubator 11 associates the calculated colony area with the elapsed time from the start of incubation for each cell line to thereby register a first calibration curve L1 with respect to a certain cell line.

The incubator 11 associates the calculated colony area with the number of cells in the colony counted according to a fluorescently-stained observation image for each cell line to thereby register a second calibration curve L2 with respect to a certain cell line as calibration curve information.

The incubator 11 associates the calculated colony area with an area per one cell in the colony for each cell line to thereby register a third calibration curve L3 with respect to a certain cell line as calibration curve information.

Before the operation start of calibration curve registration, the control unit 42 preliminarily accepts a command of a calibration curve registration operation input via the input unit 44 by the user. The command of the calibration curve registration operation includes information (cell line ID) indicating a cell line of which the calibration curve is to be registered (when the observed cell line is one cell line, the input of information (cell line ID) indicating a cell line of which the calibration curve is to be registered is not essential). The storage unit 43 preliminarily stores observation start times as an observation schedule of management data such that an observation is started after each day elapses from the elapse of one day since the start of incubation until the elapse of five days. When the method by which the user counts the number of cells in the colony is a method in which a cell in the incubation container 19 is destructed and is observed such as a counting method in which cells are fluorescently-stained and are counted according to a fluorescent observation, incubation containers 19 are prepared corresponding to the number of observation times. For example, when the observation is performed after the elapse of each of one day, two days, and three days from the start of incubation, at least three incubation containers 19 are stored in the stocker 21 of the constant temperature room 15. The same cell line is incubated in each of the incubation containers 19. By observing the incubation containers 19 one by one per one day, the cell line after the elapse of one day from the start of incubation to the cell line after the elapse of five days from the start of incubation are observed. The specific operation of preparation of the calibration curve performed by the incubator 11, that is, calculation of the colony area and registration of the calibration curve is described below. In the present embodiment, the following operation is performed by the control unit 42 included in the incubator 11; however, the following operation may be performed by a control unit externally provided on the incubator 11.

Step S101: The control unit 42 determines whether or not the observation start time of the incubation container 19 has come by comparing the observation schedule of the management data of the storage unit 43 and the current date and time. When it is the observation start time (YES), the control unit 42 forwards the process to Step S102. On the other hand, when it is not the observation time (NO), the control unit 42 waits until the next observation schedule time.

Step S102: The control unit 42 commands the container carry device 23 to carry the incubation container 19 corresponding to the observation schedule. Then, the container carry device 23 carries out the commanded incubation container 19 from the stocker 21 and places the incubation container 19 on the sample table 31 of the observation unit 22. At the timing when the incubation container 19 is placed on the sample table 31, the entire observation image of the incubation container 19 is captured by a bird view camera (not shown) embedded in the stand arm 32. Thereby, the image of the incubation container 19 including a colony image is captured. As described above, the stocker 21 is not essential. When there is no stocker 21, the step regarding the container carry is unnecessary.

Step S103: The image read unit 4203 of the control unit 42 stores the entire observation image captured in Step S102. The area calculation unit 4211 of the control unit 42 detects a colony image from the stored entire observation image and calculates the sum of areas of colony cells in the incubation container 19 or the sum of areas of colonies as the colony area.

When the calibration curve is prepared, the image of the incubation container including the colony image may be acquired, the cell number of each colony may be counted (or the cell number of each colony may be summed) from the fluorescent observation image, and the colony area may be calculated from the phase difference image. Alternatively, the total number of cells in each colony may be counted by a hemocytometer, and the colony area may be calculated from the phase difference image.

Step S104: The control unit 42 commands the container carry device 23 to carry the incubation container 19 to the small door 18 after the observation schedule is finished. Then, the container carry device 23 carries the commanded incubation container 19 to the position of the small door 18 from the sample table 31 of the observation unit 22.

Step S105: The user opens the small door 18 and takes out the incubation container 19. The user counts the number of cells according to a known method with respect to the incubation container 19 which is taken out. For example, the user counts the number of cells according to fluorescence stain. The user inputs the counted number of cells to the input unit 44. Here, the user calculates the cell density in the colony and inputs the calculated density to the input unit 44.

Step S106: The write control unit 4221 of the control unit 42 associates the cell number in the colony and the cell density in the colony input to the input unit 44 with the colony area calculated in Step S103 and the information (cell line ID) indicating the cell line to be stored in the storage unit 43. Thereby, the colony area, the cell number, and the cell line ID are associated with one another and stored in the storage unit 43 as calibration curve information (in a case of observation of one cell line, the association with the cell line ID is not essential). Then, the control unit 42 finishes the observation sequence and causes the process to return to Step S101.

The calibration curve information is stored in the storage unit 43 by repeating Step S101 to Step S106 in this way. By repeating Step S101 to Step S106 with respect to a plurality of cell lines, the calibration curve information with respect to each of the plurality of cell lines is stored in the storage unit 43. Specifically, by repeating Step S101 to Step S106 with respect to each of the cell line A and the cell line B, each of the calibration curve information of the cell line A and the calibration curve information of the cell line B is stored in the storage unit 43.

[Operation of Cell Number Estimation and Cell Quality Determination]

Figure 11:
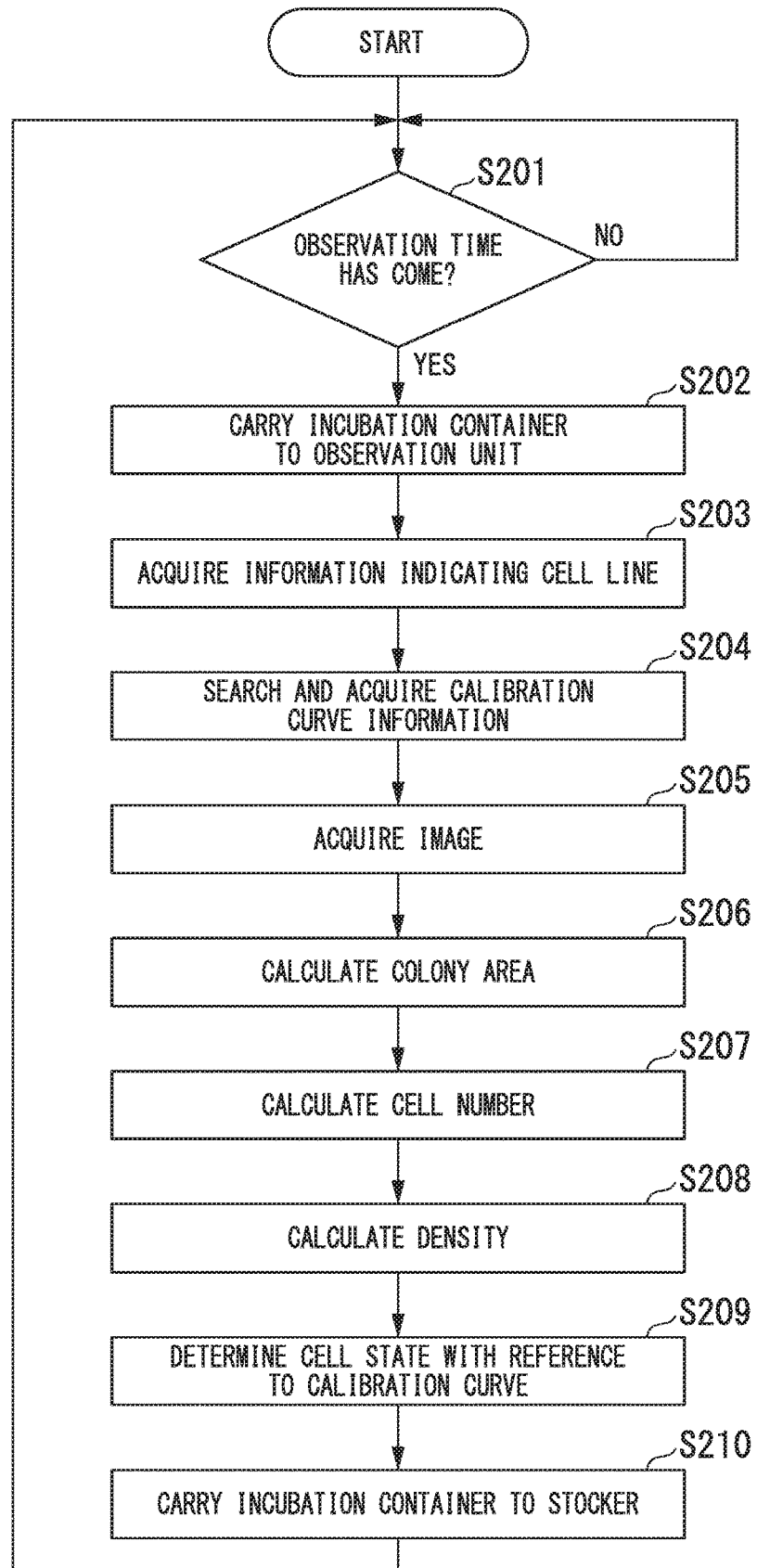
FIG. 11 is a flowchart showing an example of a cell number estimation operation according to the observation apparatus of the present embodiment.

Next, with reference to FIG. 11, an example of the cell number estimation operation of the incubator 11 is described.

FIG. 11 is a flowchart showing an example of a cell number estimation operation according to the incubator 11 (observation apparatus) of the present embodiment. In the present example, data (referred to as contrast data) regarding the number of cells against the change of the colony area of a specific cell line which is to be an observation target is acquired and is stored in advance. From the data, the determination of the quality of the observed cell is in an unknown state.

The incubator 11 performs a time lapse observation of the incubation container 19 carried in the constant temperature room 15 in accordance with the registered observation schedule. A plurality of specific types of cell lines are incubated in the incubation container 19. For example, the cell line A is incubated in an incubation container 19A of the incubation containers 19. The cell line B is incubated in an incubation container 19B of the incubation containers 19. In accordance with the observation schedule, the incubator 11 sequentially carries the incubation container 19A and the incubation container 19B to the vertical robot 38 and the observation unit 22 and captures an entire image (entire observation image) of the incubation container 19 and a microscope image in which part of the incubation container 19 is magnified. According to the registration sequence of the calibration curve information described above, the calibration curve information of the cell line A and the calibration curve information of the cell line B are stored in the storage unit 43 in advance. The operation of cell number estimation in the time lapse observation of the incubator 11 is described.

Step S201: The control unit 42 determines whether or not the observation start time of the incubation container 19 has come by comparing the observation schedule of the management data of the storage unit 43 and the current date and time. When it is the observation start time (YES), the control unit 42 forwards the process to Step S202. On the other hand, when it is not the observation time of the incubation container 19 (NO), the control unit 42 waits until the next observation schedule time.

Step S202: The control unit 42 commands the container carry device 23 to carry the incubation container 19 corresponding to the observation schedule. Then, the container carry device 23 carries out the commanded incubation container 19 from the stocker 21 and places the incubation container 19 on the sample table 31 of the observation unit 22. At the timing when the incubation container 19 is placed on the sample table 31, the entire observation image of the incubation container 19 is captured by a bird view camera (not shown) embedded in the stand arm 32.

In the present example, the observation apparatus shown in FIGS. 1, 3, and 4 is an apparatus including a constant temperature room in which a cell to be observed is incubated. Accordingly, the cell imaged in Step S202 is a cell incubated in a constant temperature room of the observation apparatus. Accordingly, the present step can be also started from the step of incubating a cell. The apparatus may not be an apparatus in which the constant temperature room is included in the observation apparatus like the present example. The apparatus may be an apparatus in which the constant temperature room for incubating a cell is separated from the observation apparatus.

Step S203: The cell number calculation unit 4222 that calculates the cell number in the colony acquires the information (cell line ID) indicating the cell line from the management data stored in the storage unit 43.

Step S204: The cell number calculation unit 4222 searches calibration curve information stored by the storage unit 43 using the acquired cell line ID as a search key and acquires calibration curve information which the cell line ID matches.

Step S205: The image read unit 4203 acquires an image captured in Step S202. The image includes an image of a colony.

Step S206: The area calculation unit 4211 calculates, based on the image acquired in Step S205, the area of the colony included in the image.

Step S207: The cell number calculation unit 4222 estimates (calculates) the number of cells based on the area of the colony calculated in Step S206 and a second calibration curve L2 of the calibration curve information acquired in Step S204.

The area calculation unit 4211 calculates the area of the recognized colony in the acquired image.

This step may be performed when a state in which observation can be made is realized after the incubation container is carried to the observation unit (S202). In this case, after the colony area is calculated, the information indicating a cell line is acquired.

Step S208: The density calculation unit 4223 calculates a cell density based on the area of the colony calculated in Step S206 and the number of cells calculated in Step S207.

Step S209: When the quality determination unit 4224 is included, the quality determination unit 4224 determines whether the colony is good or bad based on the colony area calculated from the acquired image and a first calibration curve L1 of the calibration curve information acquired in Step S204. When the quality determination unit 4224 is not included, the user determines whether the colony is good or bad based on the calculated colony area and the first calibration curve L1 of the calibration curve information acquired in Step S204.

When the maturity determination unit 4225 is included, the maturity determination unit 4225 determines the cell maturity based on the colony area calculated in Step S206, the cell density calculated in Step S208, and a third calibration curve L3 of the calibration curve information acquired in Step S204 by using the acquired image. When the maturity determination unit 4225 is not included, the user determines the cell maturity based on the colony area calculated in Step S206, the cell density calculated in Step S208, and the third calibration curve L3 of the calibration curve information acquired in Step S204.

Step S210: The control unit 42 commands the container carry device 23 to carry the incubation container 19 after the observation schedule is finished. Then, the container carry device 23 carries the commanded incubation container 19 from the sample table 31 of the observation unit 22 to a predetermined storage position of the stocker 21. Then, the control unit 42 finishes the observation sequence and causes the process to return to S201.

In addition, after it can be understood whether or not a cell is in a good state as a result of determination in Step S209, it is possible to take out a cell which is determined that the cell is in a good state from the observation apparatus and, for example, supply the cell as a cell used for drug discovery research or regenerative medicine.

By repeating Step S201 to Step S210 for each cell line in this way, the estimation result of the number of cells in each observation schedule is stored in the storage unit 43. Further, it is possible to determine whether the cell is good or bad based on the estimation result of the number of cells. Further, it is possible to supply only the selected good cell to a research institute or the like.

As described above, the incubator 11 (observation apparatus) of the present embodiment includes the cell number calculation unit 4222 that calculates, based on the calibration curve information and the colony area on the basis of the non-invasively obtained image, the number of cells included in the colony. Thereby, the incubator 11 can calculate the number of cells according to a non-invasive method and can improve the accuracy of the calculated number of cells. Further, an image obtained by a non-invasive observation (for example, phase difference observation) is used for the maturity determination or quality determination, and therefore, the determined cell can be subsequently used without obstacle for drug discovery research or regenerative medicine as a subsequent process.

The control device 41 may treat a plurality of microscope images captured during the same period of observation time of a plurality of points (for example, five points of observation or the entire incubation container 19) of the same incubation container 19 as an image of one time of the time lapse observation.

The embodiment is described using an example in which the area calculation unit 4211 detects the colony image based on the entire observation image; however, the embodiment is not limited thereto. The area calculation unit 4211 may detect the colony image by image processing of a phase difference microscope image.

A program for executing each process of the incubator 11 (observation apparatus) according to the embodiments of the invention may be recorded in a computer-readable recording medium, and the program recorded in the recording medium may be read into and executed on a computer system to thereby perform a variety of processes described above.

It is assumed that the "computer system" used herein includes an OS or hardware such as peripherals. It is also assumed that the term "computer system" includes a homepage provision environment (or a display environment) when a WWW system is used. The term "computer-readable recording medium" refers to a recordable non-volatile memory such as a flexible disk, a magneto-optical disk, a ROM, or a flash memory, a portable medium such as a CD-ROM, or a storage device such as a hard disk embedded in the computer system.

It is also assumed that the term "computer-readable recording medium" includes a medium which holds a program for a given time such as a volatile memory (for example, a DRAM (Dynamic Random Access Memory)) in the computer system which becomes a server or a client when a program is transmitted through a network such as the Internet or a communication line such as a telephone line. The program may be transmitted from the computer system which stores the program in the storage device or the like to other computer systems through a transmission medium or through transmission waves in the transmission medium. The term "transmission medium" which transmits the program refers to a medium which has a function of transmitting information, for example, a network (communication network) such as the Internet or a communication line such as a telephone line. The program may be a program which can realize part of the above-described functions. The program may be a so-called differential file (differential program) which can realize the above-described functions by a combination with a program already recorded in the computer system.

Although the embodiments of the invention has been described in detail with reference to the drawings, a specific configuration is not limited to the embodiments, and designs or the like without departing from the scope of the invention are also included.

DESCRIPTION OF THE REFERENCE SYMBOLS

11: Observation apparatus
41: Control device
4211: Area calculation unit
4222: Cell number calculation unit
4223: Density calculation unit
4224: Quality determination unit
4225: Maturity determination unit
43: Storage unit

The invention claimed is:

1. An analysis method that determines a maturity degree of a cell colony during cell incubation, comprising performing:
    an information acquisition step of acquiring information indicating a type of a cell line of which the maturity degree is to be determined;
    a calculation step of calculating, based on a captured image of a cell during the cell incubation, an area of a target colony of the cell;
    a calculation step of calculating a number of cells in the target colony based on the area of the target colony calculated in the calculation step;
    a calculation step of calculating a cell density based on the area of the target colony calculated in the calculation step and the number of cells calculated in the calculation step; and
    a step of determining a maturity degree of the target colony based on the cell density calculated in the calculation step and a calibration curve of a standard cell line that is identical to the cell line acquired in the information acquisition step.

2. The analysis method according to claim 1,
    wherein in the calculation step of calculating a number of cells, a number of cells is calculated using the area of the target colony calculated in the calculation step and a calibration curve of a standard cell line that is identical to the cell line acquired in the information acquisition step.

3. The analysis method according to claim 1,
    wherein in the information acquisition step of acquiring a type of a cell line, the type of a cell line input by a user is acquired, or the type of a cell line is acquired according to an image analysis based on a captured image of the cell line.

4. The analysis method according to claim 1,
    wherein the calibration curve of the step of determining a maturity degree indicates a relationship between an area of a colony of the cell line and an area per one cell included in the colony, and
    in the step of determining a maturity degree, the target colony is determined to be matured based on a relationship between an area per one cell included in the target colony and a predetermined threshold value relating to an area of one cell.

5. The analysis method according to claim 1, wherein information of the calibration curve for each cell line is acquired from a storage unit in which the information is stored in advance.

6. The analysis method according to claim 2, wherein information of the calibration curve for each cell line is acquired from a storage unit in which the information is stored in advance.

7. The analysis method according to claim 1, further comprising
a step of determining whether the colony is good or bad based on the area of the target colony calculated in the calculation step and a calibration curve of a standard cell line that is identical to the cell line.

8. An observation apparatus, comprising:
an imaging device that captures a cell incubated in an incubation container;
an information input interface that permits information to be input indicating a type of a cell line of which a maturity degree is to be determined; and
a controller unit to which each of the imaging device and the information input interface is connected, wherein the controller is programmed to:
calculate, based on an image of the cell during incubation captured by the imaging device, an area of a target colony of the cell;
calculate a number of cells in the target colony based on the calculated area of the target colony;
calculate a cell density based on the calculated area of the target colony and the calculated number of cells; and
determine a maturity degree of the target colony based on the calculated cell density and a calibration curve of a standard cell line that is identical to the input cell line information.

9. The observation apparatus according to claim 8, wherein the number of cells in the target colony is calculated using the area of the target colony calculated by the area calculation unit and a calibration curve of a standard cell line that is identical to the input cell line information.

10. The observation apparatus according to claim 8, wherein the information input interface acquires the type of a cell line input by a user or acquires the type of a cell line according to an image analysis based on the captured image of the cell line.

11. A non-transitory, computer-readable storage medium that stores a program that causes a computer to execute:
an information acquisition step of acquiring information indicating a type of a cell line of which the maturity degree is to be determined;
a calculation step of calculating, based on a captured image of a cell during incubation, an area of a target colony of the cell;
a calculation step of calculating a number of cells in the target colony based on the area of the target colony calculated in the calculation step;
a calculation step of calculating a cell density based on the area of the target colony calculated in the calculation step and the number of cells calculated in the calculation step; and
a step of determining a maturity degree of the target colony based on the cell density calculated in the calculation step and a calibration curve of a standard cell line that is identical to the cell line acquired in the information acquisition step.

* * * * *